United States Patent [19]
Iguchi

[11] 4,118,752
[45] Oct. 3, 1978

[54] APPARATUS FOR INFLICTING ELECTRIC INJURY UPON LAND SHELLFISH SUCH AS SNAILS AND THE LIKE

[76] Inventor: Shozo Iguchi, 1-6, Roppongi 5-chome, Minato-ku, Tokyo, Japan

[21] Appl. No.: 792,268

[22] Filed: Apr. 29, 1977

Related U.S. Application Data

[63] Continuation-in-part of Ser. No. 654,177, Feb. 2, 1976, abandoned.

[51] Int. Cl.² ............................................. H05C 1/04
[52] U.S. Cl. ...................................... 361/232; 256/10
[58] Field of Search ...................... 361/232; 256/1, 10

[56] References Cited
U.S. PATENT DOCUMENTS

| | | | |
|---|---|---|---|
| 2,400,869 | 5/1946 | Kennedy | 361/232 |
| 3,868,545 | 2/1975 | Caron | 361/232 |

FOREIGN PATENT DOCUMENTS 443,773  2/1968  Switzerland .............................. 361/232

*Primary Examiner*—R. N. Envall, Jr.
*Attorney, Agent, or Firm*—Wallenstein, Spangenberg, Hattis & Strampel

[57] ABSTRACT

An apparatus for collecting shellfish and the like comprises a first fence anchored in the ground to enclose a collection area, said fence comprising wall sections of a height to be scaled by shellfish, each of said wall sections having exposed on only the inner surface thereof a pair of vertically spaced conductors spaced less than the length of the shellfish and so as to be in the advancing path of the shellfish scaling the wall section from the inner side thereof. Means are provided for applying intermittent voltage pulses continuously to the conductors which pulses are spaced apart a time interval less than the time required for the shellfish to span the space therebetween.

4 Claims, 12 Drawing Figures

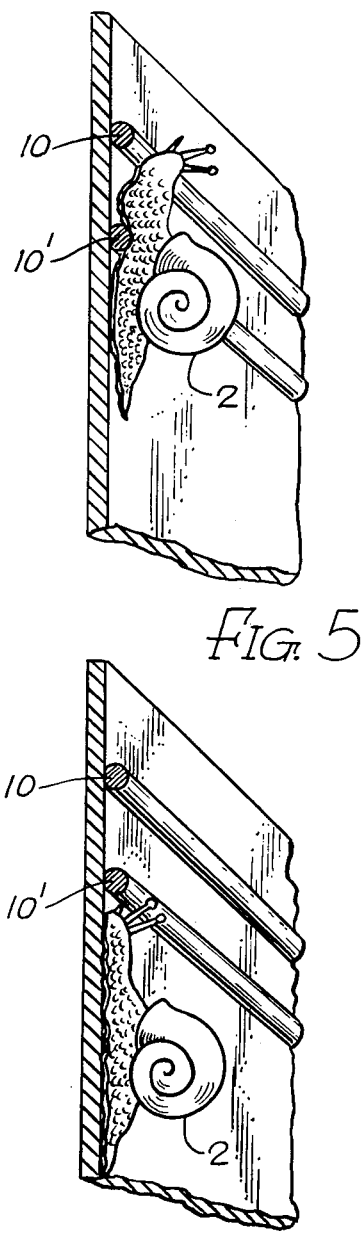
FIG. 5
FIG. 3
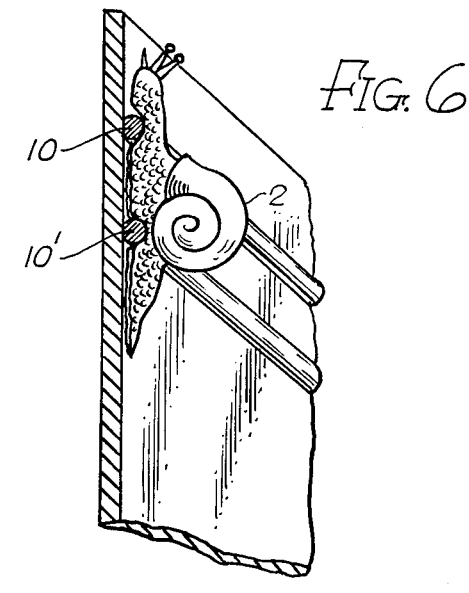
FIG. 6
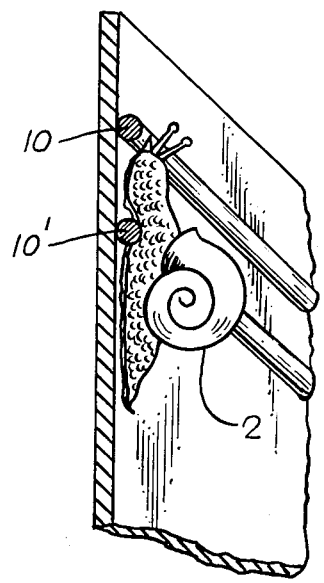
FIG. 4

4,118,752

APPARATUS FOR INFLICTING ELECTRIC INJURY UPON LAND SHELLFISH SUCH AS SNAILS AND THE LIKE

RELATED APPLICATION

This application is a continuation-in-part of Application Ser. No. 654,177 filed on Feb. 2, 1976, now abandoned.

BACKGROUND OF THE INVENTION

This invention relates in general to an apparatus for inflicting electric injury upon land shellfish such as snails, slugs and the like and other living things harmful in agriculture.

Heretofore, in order to protect the crops and the like from living things harmful in agriculture represented by land shellfish like snails, there was a method of enveloping an area to be protected entirely with a wall and applying a coating on the wall surface with a chemical substance for repelling such harmful living things, but these methods were not effective because of the cost of equipment therefor being high or the aspect of efficacy being questionable. Also, a method for protecting such area electrically from harmful living things was likewasie proposed. In this so-called electric fence method the area to be protected is encircled with an electric fence comprising a pair of conductors and a high-voltage (for example, merely a voltage of 110 V for commercial use) is applied to such conductors. Because of this high-voltage current, the greater part of harmful living things are either killed by an electric shock or at least deprived of their ability to move into the area involved. In this sense, the method of using such electric fence is effective, but is not reliable and rugged and, because of the high-voltage utilized, the danger to men and beasts is great.

An approach to keeping snails or the like out the a protected area is disclosed in Swiss Pat. No. 443,773, granted Feb. 15, 1968. In this patent, a pair of horizontally spaced insulating conductors are laid on the ground and pulses of voltage are applied thereto in a manner which will kill or shock the snails as they bridge the conductors. This means of protecting an area from shellfish and the like has the disadvantage that when the snails are not killed, they are undesirably still free to roam in the area involved to cause a nuisance, even though they may not be able to enter a given protected area.

It is an object of the present invention to provide means for protecting a given area against the intrusion of shellfish or the like without danger to human beings and wherein the shellfish are not killed but are rather trapped within a defined area.

Accordingly, this invention has for its object the elimination of one or more of the above-mentioned disadvantages of the electric fence.

SUMMARY OF THE INVENTION

In the preferred form of the invention, a fence is constructed enclosing a snail collection area where one pair of vertically spaced shocking conductors are exposed only on the inside of the fence. Across these conductors are applied relatively low voltage pulses having a predetermined pulse rate and pulse duration. For example, short pulses (for example, 1.5 seconds duration) spaced apart relatively long intervals (for example, 25 seconds) are used, so that the average current which flows into the conductor pair becomes extremely small, and, accordingly, no problems of a safety hazard, large leakage current or corrosion occur, as in the conventional apparatus. The amplitude of the voltage pulses can be of a relatively small value (for example, 30 V). Because of the interval between the pulses, the shellfish can move fully over the conductors before receiving any shock, so its shrinkage reaction will cause the shellfish to drop from the fence when shocked thereby. Thus, shellfish can pass over the fence to enter a seizing area within the confines of the fence. The shellfish are collected in the seizing area since any shellfish which attempts to climb out of the area are shocked and so fall into the seizing area. The shellfish in the seizing area can be retained live so long as the voltage applied to the two conductor pairs is not fatal to such shellfish.

DESCRIPTION OF DRAWINGS

FIGS. 3 through 6 illustrates the different positions of a snail climbing up over one of the wall sections of the fence shown in FIGS. 1 and 2 when a snail progressively approaches and then completely symmetrically bridges two vertically spaced conductors on the inside surface of the fence section;

DESCRIPTION OF PREFERRED EMBODIMENT OF THE INVENTION

Figure 1:
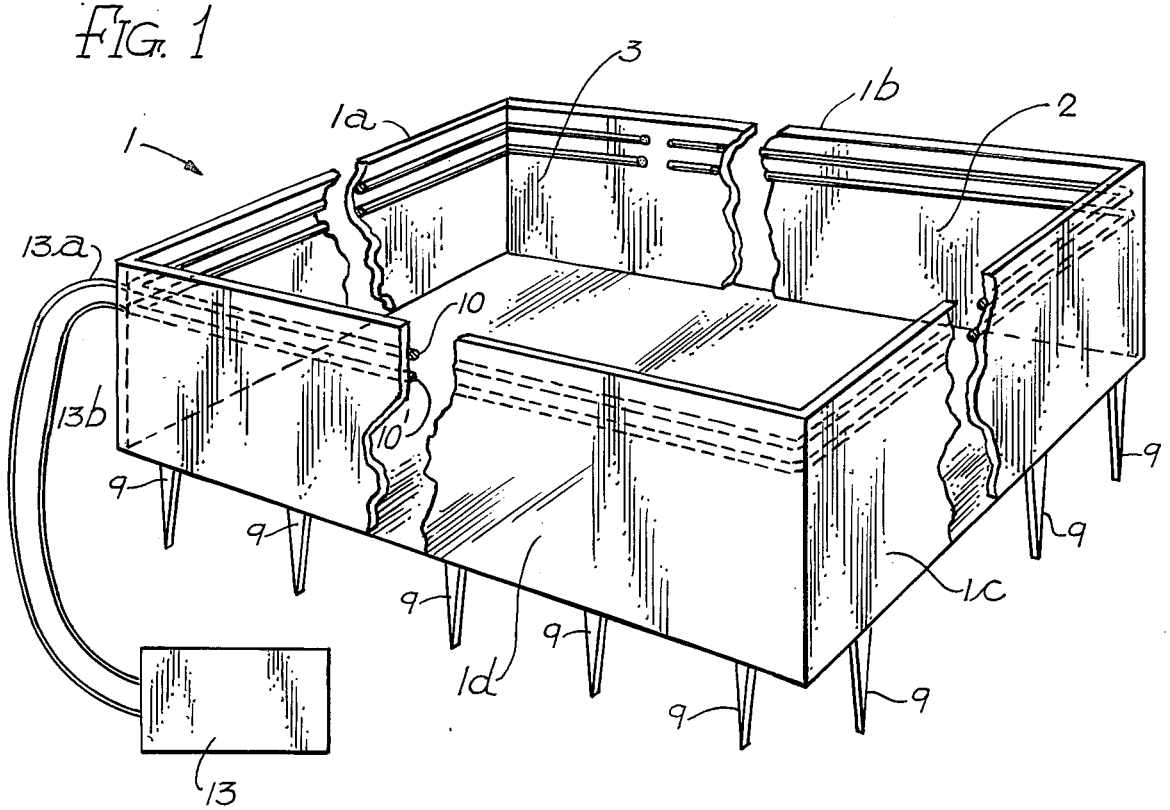
FIG. 1 is a prospective view of a fencing system of the present invention which encloses a shellfish collecting area.
Figure 2:
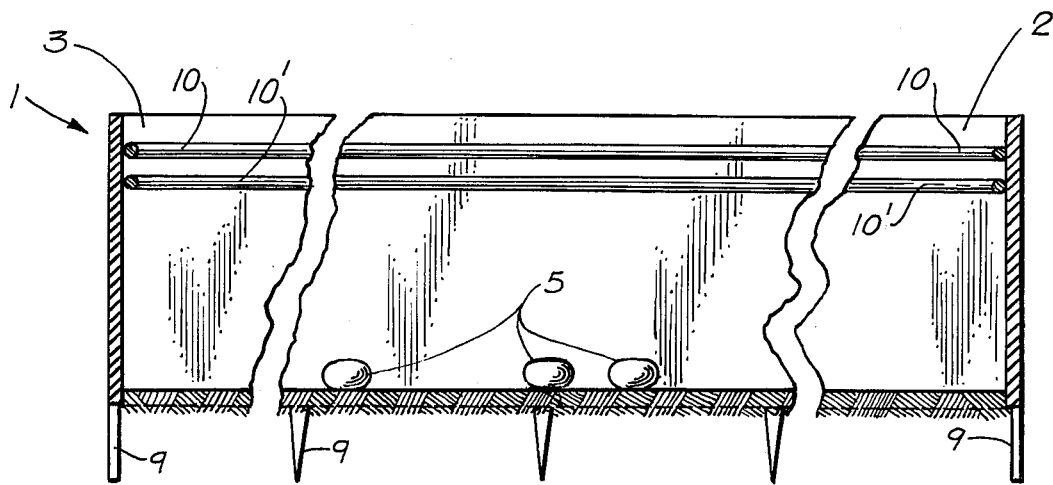
FIG. 2 is a vertical sectional view through the fencing system shown in FIG. 1.
Figure 8:
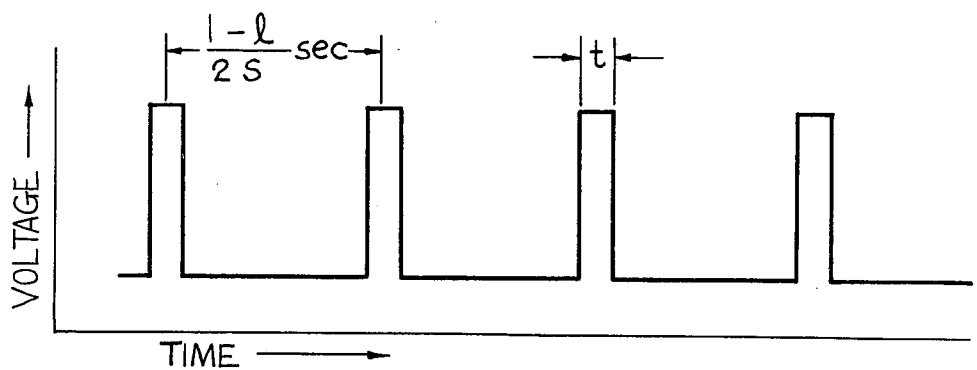
FIG. 8 shows the waveform of the voltage pulse train applied to the conductors of the fence, and also shows the formula for relating the preferred timing between successive pulses and the dimensions shown in FIG. 7.

FIG. 1 illustrates a fencing system 1 enclosing a space 3 to which snails 2 are to be collected. This fencing system can include the four separate wall sections 1a, 1b, 1 and 1d which may be made of an insulating synthetic plastic material. The wall sections are shown falling along the outlines of a rectangular, as shown in FIGS. 1 and 2, or they could be single generally circular spaced or oval-shaped wall or wall sections enclosing a circular collection space. Within the collection space 2 is placed a suitable shellfish attracting substance 5. Where the shellfish involved are snails, this material could be beer yeast. Anchored upon the corresponding points of the inner surface of each of the wall sections 1a, 1b, 1c and 1d are a pair of vertically spaced parallel horizontal exposed metal conductors 10 and 10'. Each of the wall sections 1a, 1b, 1c and 1d have at regular intervals therealong downwardly projecting stakes 9 for anchoring the wall sections into the ground at various points therealong. The distance between the conductor pairs 10—10' on each of the wall sections is selected to be smaller than the total length of the particular shellfish 2 involved, which are shown as snails in the drawings. A pulse generator 13 is provided which generates on a pair of output conductors 13a–13b a train of voltage pulses which may be like that shown in FIG. 8. The output conductors 13a–13b extend respectively to the vertically spaced conductors 10—10' on the various wall sections.

Snails outside of the collection space 3 attracted by the snail attracting substance 5 climb one of the wall sections 1a, 1b, 1c and 1d into the collection space 3. When the snail attempts to climb out of the collection space 3 and reaches the point shown in FIG. 6, the resulting applied electrical voltage to the vertical conductors will cause the snail to contract and to fall into the collection space.

If a continuous sinusoidal potential difference were to be applied to the conductor pairs, then, when the snail 2 is about to pass thereacross (FIG. 4), it would immediately receive an electric shock due to its gastropod bridging the conductor pair, at which moment the snail's reflexes quickly separate the upper end portion of its gastropod from the conductor 10 quickly to shorten the time of the voltage application to as little as 30 mili-seconds. To inflict sufficient shock upon the snail in a short time of its reacting on this electric shock to cause the snail to contract to a point to fall from the fence, it would be undesirably necessary to have a dangerous high voltage normally applied. However, if widely spaced pulses are applied, as shown in FIG. 2, the snail 2 can bridge the conductor pair fully as in FIG. 6 so there when a voltage pulse is suddenly applied between the conductors 10 and 10, the shellfish cannot as quickly leave contact with the conductors as it contracts, and so will be shocked to an extent to cause it to fall from the fence.

Figure 7:
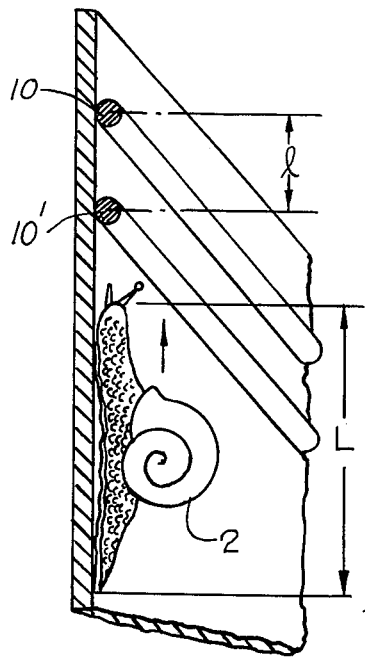
FIG. 7 is a view showing the shellfish in the position shown in FIG. 3, with various dimensions marked thereon.
Figure 10:
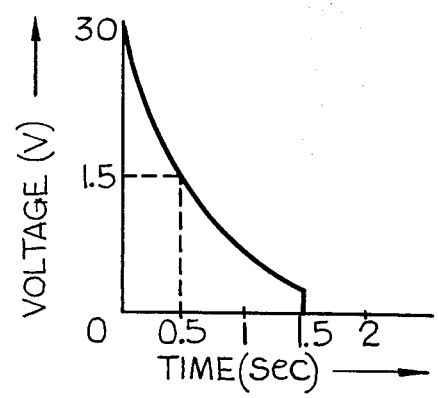
FIG. 10 is a diagram showing an output pulse produced by the circuit of FIG. 9.

FIG. 7 is a diagram for determining an exemplary electric pulse interval and duration in accordance with this invention. If the length in advancing direction of land shellfish 2 which are made the objects is taken as L, the advancing speed as S per second, and the distance between a pair of conductors 10 and 10' as 1, then the time for the land shellfish to pass over and bridge the conductors is (L − 1)/S second, so that, if an electric current is applied at intervals of about ½ thereof, then, in almost all cases, it becomes possible to have the land shellfish struck by electricity in the state close to that in FIG. 6.

Figure 9:
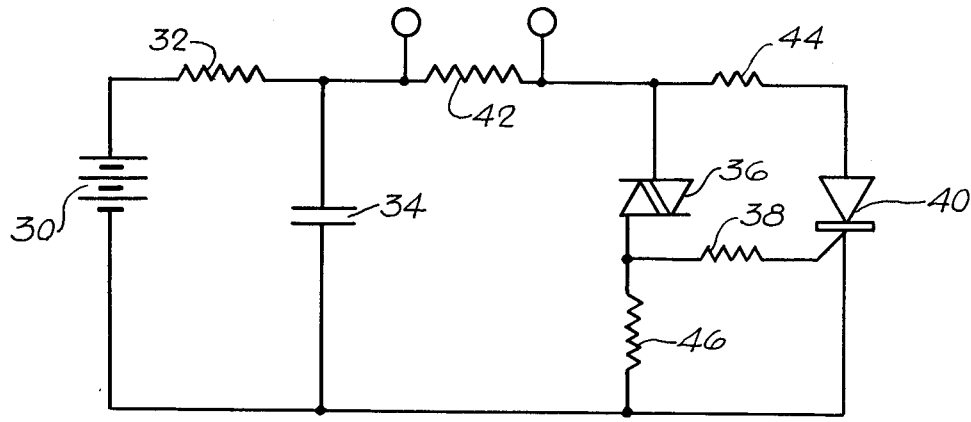
FIG. 9 is a circuit diagram showing one embodiment of the longitudinal pulse generating circuit which could be used with the present invention.

FIG. 9 shows a pulse generating circuit designed to inflict non-fatal injury upon medium-sized snails. A DC voltage source 30 of about 30 V is used in this circuit. The electric current from the source 30 builds up a charge on capacitor 34 (e.g., of 70 micorfarads) through a resistor 32 (e.g., 70,000 ohms). When the charged on the capacitor 34 reaches the break-over voltage of a trigger diode 36, pulses are applied to the gate of a thyristor 40 through a protective resistor 38 (e.g., of 50 ohms), whereby the thyristor 40 is turned on. When the thyristor is turned on, an electric current flows through an output resistor 42 of 5,000 ohms, a protective resistor 44 (e.g., of 50 ohms) and the thyristor 40. The momentary value of this current is proportional to the momentary charge amount of the capacitor 34, and, accordingly, if the current which flows through the thyristor 40 decreases to the momentary charge amount of the capacitor 34 corresponding to the holding current of the thyristor 40, the thyristor 40 is turned off. When the thyristor 40 is turned off, the capacitor 34 is recharged through the resistor 32. This sequence is carried out repeatedly, so that, at both ends of an output resistor 42, a voltage is generated periodically. A resistor 46 between the trigger diode 36 and common conductor 49, which may have a value of 2,000 ohms acts as a protective resistor.

In the above construction, the pulse interval is determined by the values of the resistor 32 and the capacitor $C_1$, and the pulse duration is determined by the values of the output resistor 42 and the capacitor 34. When the constants (parameters) of the circuit elements mentioned above are used, the output waveform (single pulse waveform) becomes as in FIG. 9, that is, the pulse interval becomes about 25 seconds, the pulse duration becomes about 1.5 seconds, and the peak output voltage becomes about 30 V.

Figure 11:
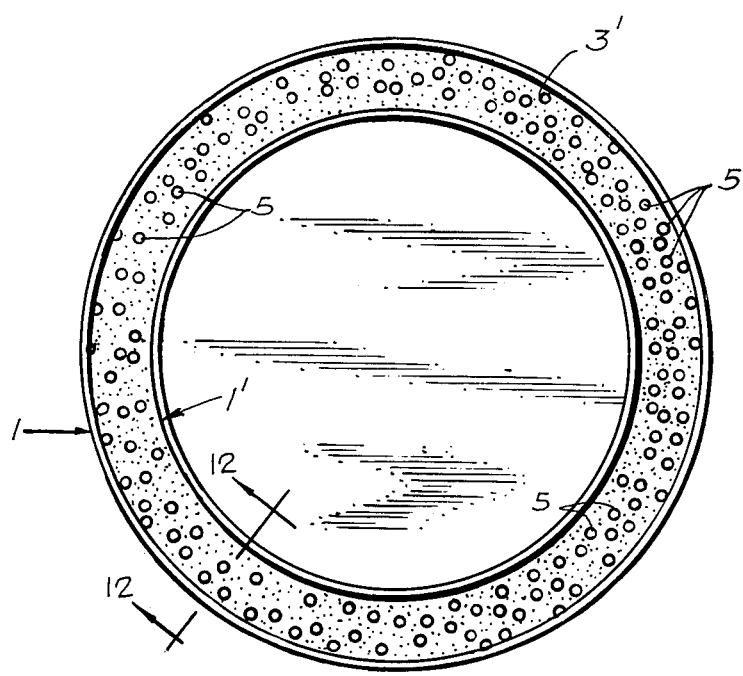
FIG. 11 illustrates an alternative embodiment of the invention wherein the shellfish collection apparatus comprises concentrically located circular fences spaced apart to define an annular shellfish collecting area therebetween.
Figure 12:
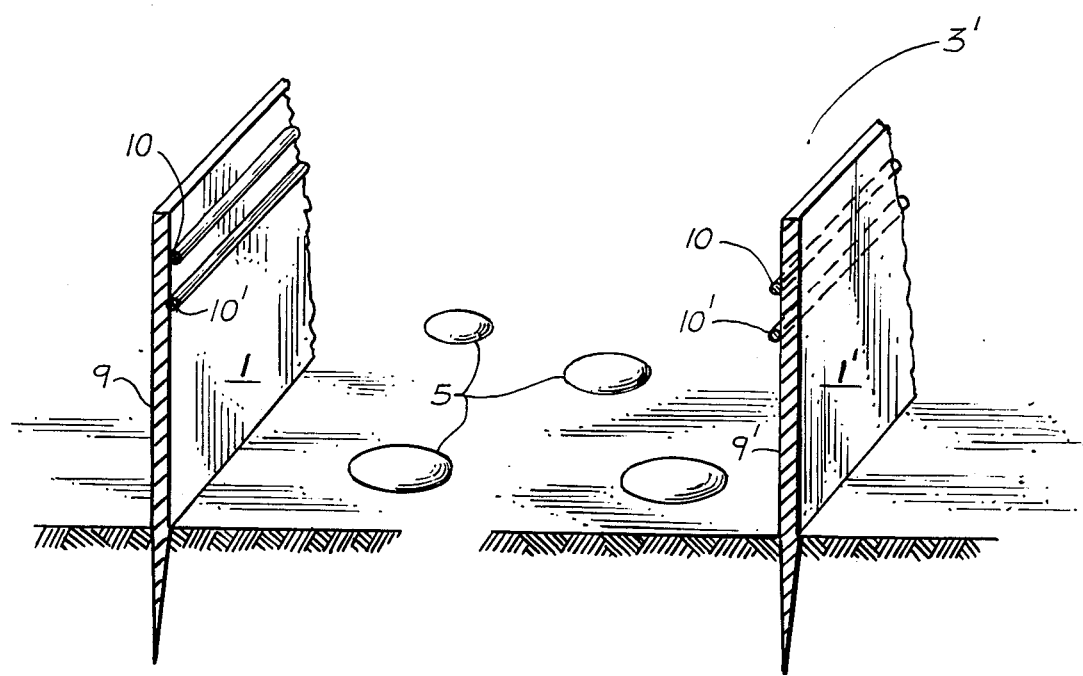
FIG. 12 is a greatly enlarged fragmentary sectional view through a portion of the fence construction shown in FIG. 11.

Instead of utilizing one or more stake carrying fence-forming wall sections which enclose within the entire confines thereof a collecting space 3 as shown in FIGS. 1 and 2, an annular collection space 3' may be provided between two spaced circular wall sections 1—1' shown in FIGS. 11 and 12, each having a pair of vertically spaced conductors 10—10' as in the embodiment shown in FIGS. 1 and 2. The vertically spaced conductors 10—10' are exposed only on the confronting inner spaces of the wall sections 1 and 1'. The space within the innermost wall 1' will thus be free of the shellfish 2.

I claim:

1. An apparatus for collecting shellfish, comprising: a shellfish collection enclosure to enclose a collection area, said enclosure comprising insulating wall means of a height to be scaled by the shellfish, said wall means having exposed on only the inner surface thereof a pair of exposed vertically spaced conductors spaced less than the length of the shellfish and horizontally extending over the length of the wall means so as to be in the advancing path of the shellfish scaling the wall means from inside the enclosure, and means for applying intermittent voltage pulses of a value which are not hazardous to humans continuously to said conductors which pulses are spaced apart a time interval less than the time required for the shellfish to traverse the space therebetween.

2. The apparatus of claim 1 wherein said voltage pulses are spaced apart a time interval many times the duration of each of the voltage pulses.

3. The apparatus of claim 1 wherein the duration of said pulses is sufficient to, at least, incapacitate the shellfish and wherein the spacing of said conductors is much less than the length of the shellfish and the interval between the pulses is sufficiently great that if the living thing receives an initial pulse as it first bridges the pair of conductors the next pulse will occur at a point where the living thing substantially overlaps the conductors to an extent where it reflex action will cause such a reaction that the shellfish will drop from the wall means involved.

4. The apparatus of claim 1 wherein there is a second enclosure like said first enclosure but located within said first enclosure to define a collection area between the enclosures and a shellfish free area within said second enclosure, said second enclosure having its vertically spaced conductors exposed only on the surfaces thereof facing the inner surfaces of the first enclosure and connected to said voltage applying means whereby the shellfish can climb over the wall means of the first enclosure into said collection area but cannot then climb over the wall means of either enclosure.

* * * * *